United States Patent [19]

Farren

[11] Patent Number: 4,618,771

[45] Date of Patent: Oct. 21, 1986

[54] NON-DISPERSIVE INFRARED ANALYZER HAVING IMPROVED INFRARED SOURCE AND DETECTING ASSEMBLIES

[75] Inventor: Carl A. Farren, Placentia, Calif.

[73] Assignee: Beckman Industrial Corporation, Fullerton, Calif.

[21] Appl. No.: 551,454

[22] Filed: Nov. 14, 1983

[51] Int. Cl.$^4$ .............................................. G01J 1/00
[52] U.S. Cl. .................................... 250/343; 250/345
[58] Field of Search ............ 250/343, 345, 353, 493.1, 250/504 R; 350/630, 628, 1.1

[56] References Cited

U.S. PATENT DOCUMENTS

| | | | |
|---|---|---|---|
| 1,692,413 | 11/1928 | Lewis | 313/35 |
| 2,942,260 | 6/1960 | Carter | 343/781 P |
| 3,108,173 | 10/1963 | Barrett et al. | |
| 3,532,417 | 10/1970 | Tiemann | 350/630 |
| 3,551,676 | 12/1970 | Runnels | 250/353 |
| 3,619,562 | 11/1971 | Jacobs | |
| 3,694,624 | 9/1972 | Buchta | |
| 3,761,678 | 9/1973 | Eckles | |
| 3,784,836 | 1/1974 | Tolliver | |
| 3,871,751 | 3/1975 | Rambauski et al. | 350/630 |
| 3,911,277 | 10/1975 | Cederstrand et al. | |
| 3,920,993 | 11/1975 | Cederstrand et al. | |
| 4,013,892 | 3/1977 | Udart | |
| 4,148,298 | 4/1979 | Sherman | 126/270 |
| 4,317,042 | 2/1982 | Bartell | |
| 4,320,297 | 3/1982 | Cederstrand et al. | |
| 4,331,878 | 5/1982 | Steinmetz | |
| 4,355,233 | 10/1982 | Warnke et al. | |

FOREIGN PATENT DOCUMENTS 2603879 8/1977 Fed. Rep. of Germany ...... 350/630
2720063 11/1978 Fed. Rep. of Germany ...... 250/504

OTHER PUBLICATIONS

Strong et al, "Procedures in Experimental Physics" 1938, pp. 378-397.
Burkhard et al, "Reflective Optics System for Multiple Beam Laser Fusion" *Applied Optics*, May, 1983, vol. 22, #9, p. 1313.

Primary Examiner—Bruce C. Anderson
Assistant Examiner—Richard Hanig
Attorney, Agent, or Firm—John E. Vanderburgh

[57] ABSTRACT

An improved non-dispersive infrared analyzer. The analyzer includes an improved source assembly having a reflecting element with a concave annular reflecting surface, and a circular heating element which is located substantially at the focal region of the reflective surface. The analyzer also includes an improved detecting assembly having a reflecting element with a paraboloid reflective surface that focuses radiation on one or more detecting elements that are located out of the field of view of the reflecting element. Because of the better collimation and more efficient use of its infrared beam, analyzers which include these source and detecting assemblies may use sample cells having non-reflective inner surfaces, and thereby provide output signals of improved stability.

27 Claims, 9 Drawing Figures

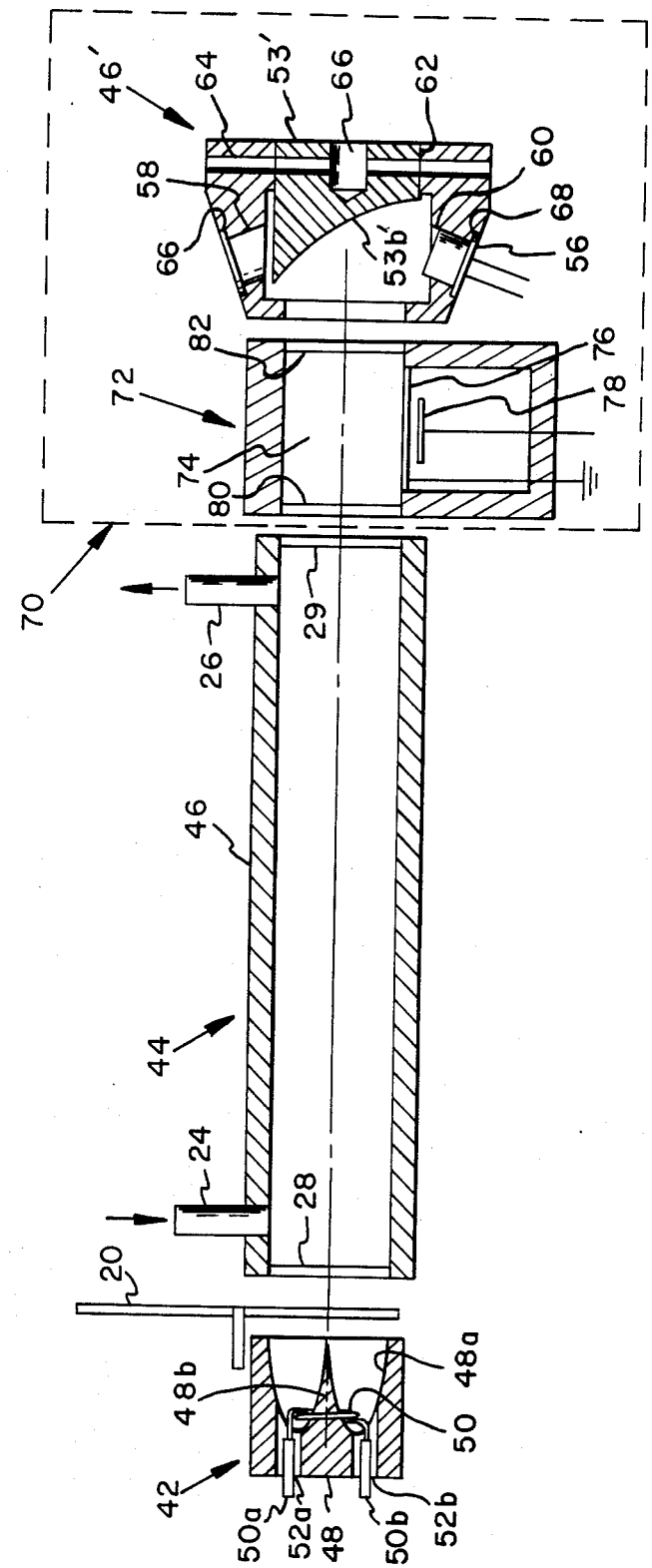

NON-DISPERSIVE INFRARED ANALYZER HAVING IMPROVED INFRARED SOURCE AND DETECTING ASSEMBLIES

BACKGROUND OF THE INVENTION

The present invention relates to non-dispersive infrared analyzers and is directed more particularly to non-dispersive infrared analyzers having improved infrared source and detecting assemblies.

Instruments which measure the concentration of a component of interest of a sample gas often operate by measuring the quantity of infrared radiation that is absorbed by the sample gas as the latter flows through a sample cell that is irradiated by a beam of infrared radiation of known intensity. By measuring the amount of radiation that is transmitted through the sample cell at wavelengths that are characteristic of the component of interest, the amount of radiation that is absorbed by the sample gas at such wavelengths, and therefore the concentration of the component of interest, may be determined. This transmitted radiation may be measured by any of a number of different types of infrared detecting elements such as thermistors, Luft-type detectors, etc.

Infrared analyzers of the above type are classified on the basis of the numbers and types of sources, gas containing cells and infrared detecting elements used therein. Examples of analyzers which use a single source, a single gas containing cell, and a plurality of infrared detecting elements are described in U.S. Pat. No. 3,920,993, issued on Nov. 18, 1975 in the name of Cederstrand et al., and in U.S. Pat. No. 4,320,297, issued on Mar. 16, 1982 in the name of Cederstrand et al. An example of an analyzer which uses two infrared sources, two gas-containing cells and a single infrared detecting element is described in U.S. Pat. No. 4,355,233, issued on Oct. 19, 1982 in the name of Warnke et al. An analyzer which makes use of a single infrared source, two gas containing cells and one or more infrared detecting elements is described in U.S. Pat. No. 4,467,213 issued Aug. 21, 1984 in the name of C. A. Farren.

In order to assure high sensitivity and a high signal-to-noise ratio, non-dispersive infrared analyzers are designed so that as much infrared radiation as possible is transmitted from the source to the detecting element. In order to accomplish this, such an analyzer is often provided with a source assembly having a parabolic reflector with an infrared heating element located as nearly as possible at the focal point thereof, and with a sample cell having highly reflective interior walls. In addition, if the analyzer uses solid-state detecting elements, it is often provided with a detecting assembly having a parabolic reflector for focusing the radiation that emerges from the sample cell onto one or more infrared detecting elements that are located as nearly as possible at the focal point thereof.

While an analyzer of the above-described type is adequate for many applications, it has limitations which prevent it from realizing its full potential sensitivity and stability. One of these is that the infrared heating element used therein is not sufficiently small and point-like to assure that its source assembly emits a well collimated beam of radiation. As a result, a substantial fraction of the radiation that is emitted by the source assembly either does not enter the gas containing cell or is transmitted through that cell only after multiple reflections from the inner surface thereof. These multiple reflections, in turn, cause the overall quantity of radiation that is transmitted through the cell to be strongly affected by the presence of dirt on the inner surface thereof. This result is highly undesirable because it causes the output signal of the detecting element to drift with time as the flow of the sample gas deposits dirt on the inner surface of the cell.

Another limitation of analyzers of the above-described type is that the non-collimated or off-axis component of the infrared beam (i.e., the component of the beam which is not parallel to the optical axis of the analyzer) is not properly focused on the detecting element by the parabolic reflector of the detecting assembly. This occurs because the off-axis component of the beam does not strike the surface of the reflector at the proper angle for reflection to the focal point thereof. The total amount of radiation that is received by the detecting element is further reduced by the blocking effect of the structures which are used to mount the detecting element.

In summary, non-dispersive infrared analyzers of types that were used prior to the present invention had low sensitivities and stabilities which resulted from the use of inefficient source, sample cell and detecting assemblies.

SUMMARY OF THE INVENTION

In accordance with the present invention there is provided a non-dispersive infrared analyzer which incorporates a number of improvements that increase the efficiency with which infrared radiation is generated, transmitted and detected. As a result of the combined effect of these improvements, both the sensitivty and the stability of the analyzer of the invention are substantially greater than those of previously known analyzers.

In accordance with one feature of the present invention, there is provided an improved source assembly that produces an infrared beam having an intensity and a degree of collimation which are greater than those of previously used source assemblies. This source assembly includes an improved reflecting element having a reflecting surface which lies in the surface of revolution produced by the rotation of a concave shape about an axis that is offset from the axis of the cell which it is to illuminate. The source assembly of the invention also includes an improved heating element which cannot only be made longer than previously used elements, but which can be confined to a smaller volume that more nearly coincides with the focal region of the reflecting element. Because the heating element is longer, the source assembly can generate a more intense beam of infrared radiation without increasing the operating temperature of the heating element and thereby reducing its useful life. In addition, because the heating element more nearly coincides with the focal region of the reflecting element, the source assembly can produce an infrared beam having a higher degree of collimation. Together these improvements substantially increase the efficiency of the source assembly without appreciably increasing its cost.

In accordance with another feature of the present invention, there is provided an improved detecting assembly that increases the amount of infrared radiation that can be focussed upon the infrared detecting elements. This detecting assembly includes an improved reflecting element having one or more off-axis reflective surfaces and one or more detecting elements that are located at the focal points of these off-axis surfaces.

Because of the use of off-axis surfaces, the detecting assembly need not use detecting element mounting structures which tend to block a part of the infrared radiation that is to be focused thereon. As a result, the detecting assembly of the invention collects a greater percentage of the infrared radiation that emerges from the sample cell than previously known detecting assemblies. This increase in received radiation, in turn, increases both the sensitivity and signal-to-noise ratio of the analyzer.

Because of the above-discussed improvements in the source and detecting assemblies, the analyzer of the invention is less dependent upon the reflection of infrared radiation from the inner surface of the sample cell than previously used analyzers. This lessened dependency, in turn, makes it possible to use sample cells having non-reflective (i.e., unpolished) inner surfaces. This not only reduces the cost of the sample cell, but also reduces the extent to which the output of the analyzer is affected by the deposition of dirt on the inner surface thereof. As a result, the output of the analyzer of the invention is more stable than the outputs of analyzers having samples cells that have highly polished inner surfaces.

DESCRIPTION OF THE DRAWINGS

Other objects and advantages of the present invention will be apparent from the following description and drawings in which:

FIG. 6 is a cross-sectional view of an alternative embodiment of the analyzer of the invention.

DESCRIPTION OF THE PREFERRED EMBODIMENTS

Figure 1:
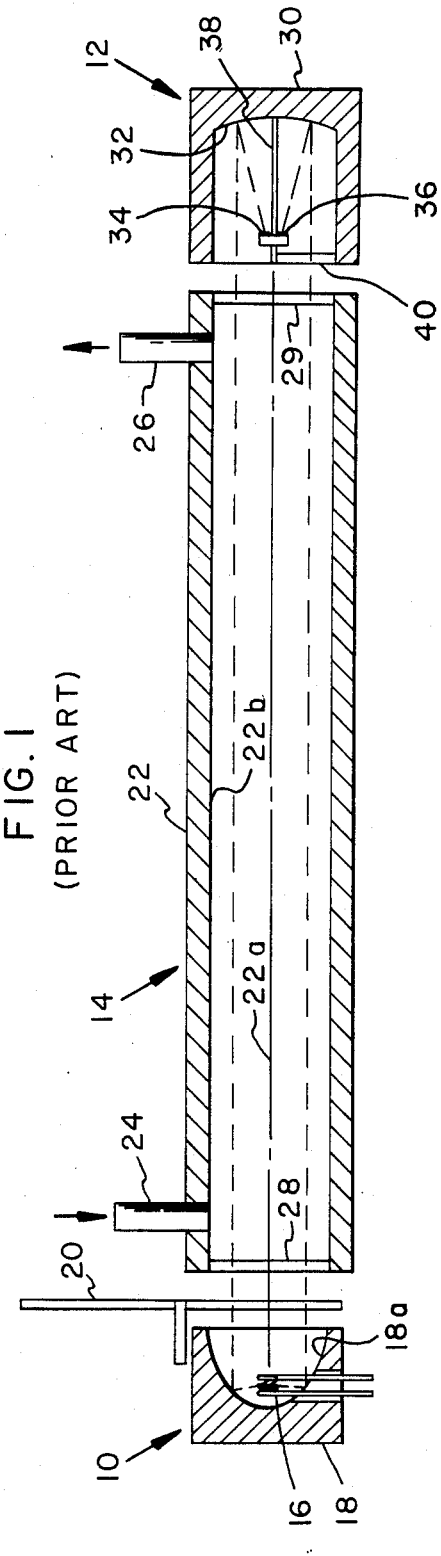
FIG. 1 is a cross-sectional view of a non-dispersive infrared analyzer of a type known in the art.

Referring to FIG. 1, there is shown a simplified cross-sectional view of the optical portion of an infrared analyzer of a type which is known in the art. This analyzer includes a source assembly 10 for directing a beam of infrared radiation onto a detecting assembly 12, through a sample cell assembly 14. For a given intensity of the infrared beam produced by source assembly 10, the radiation received by detecting assembly 12 is related to the concentration of the component of interest in the sample gas within cell assembly 14. As a result, the output signal of detecting assembly 12 may be used as a measure of the concentration of that component of interest.

Source assembly 10 typically includes an electrically powered heating element 16 which comprises several turns of a wire that can withstand the temperatures necessary to generate the desired flux of infrared radiation. Source assembly 10 also includes a reflecting element 18 having an inner reflective surface 18a for directing the radiation emitted by heating element 16 along the axis 22a of cell assembly 14. By imparting to surface 18a the shape of a paraboloid (i.e., the shape generated by a parabola that has been revolved about its axis) and by locating heating element 16 at the focal point of that paraboloid, a substantial fraction of the radiation from source assembly 10 may be emitted in a beam that is exactly parallel to axis 22a of cell assembly 14. Before this beam is incident on the cell assembly, however, it is preferably interrupted at a low frequency, such as 10 Hz, by interposing a rotating chopper blade 20 between the source assembly and the cell assembly. Because the purpose of and drive circuitry for chopper 20 are well known to those skilled in the art, they will not be further described herein.

Sample cell assembly 14 typically comprises a tube-like cell body 22 having an inlet 24 and outlet 26 through which the sample gas may be pumped by a conventional gas sampling apparatus not shown. The ends of this tube-like body are closed by suitable infrared transparent windows 28 and 29. In order to assure the maximum possible transmission of both the on-axis and off-axis components of the infrared beam, the inner surface 22b of cell body 22 is preferably highly polished, and then plated with a corrosion-resistant material such as gold.

Detecting assembly 12 typically includes a reflecting element 30 having a reflecting surface 32 which has the shape of a paraboloid. This reflecting surface serves to concentrate the beam of infrared radiation received from cell assembly 14 onto one or more infrared detecting elements, such as 34 and 36, which may comprise thermistors or other solid state infrared energy responsive devices. These detecting elements are located as nearly as possible at the focal point of the reflecting surface 32 by a suitable mounting structure 38. The mounting structure shown in FIG. 1 is of the type shown in greater detail in previously-cited U.S. Pat. No. 4,320,297.

When, as is the case in FIG. 1, the analyzer includes only a single gas containing cell, the use of two detecting elements, such as 34 and 36, is desirable so that one part of the infrared beam may be focused onto one detecting element to serve as a reference beam, while another part is focused on the other detecting element to serve as a measuring beam. The difference in the spectral response that allows the output of the measuring detector to be referenced to the output of the reference detector is produced by locating a suitable infrared band pass filter 40 optically upstream of the detector which is to be used as the measuring detector. Because signal processing circuitry which can be used to produce the desired analyzer output signal from the outputs of the measuring and reference detectors is well known, it will not be shown or described herein.

Figure 2:
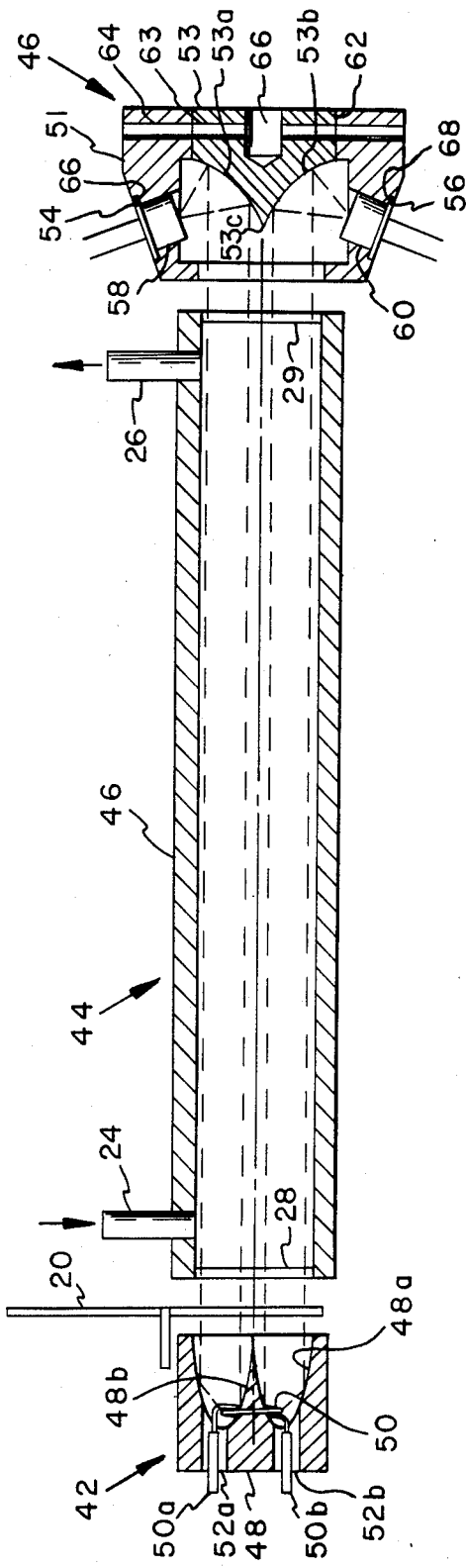
FIG. 2 is a cross-sectional view of one embodiment of a non-dispersive infrared analyzer that has been constructed in accordance with the present invention.

Referring to FIG. 2, there is shown a simplified cross-sectional view of one embodiment of an infrared analyzer that has been constructed in accordance with the present invention. Generally speaking, the analyzer of FIG. 2 includes a source assembly 42, a cell assembly 44 and a detecting assembly 46 which have functions that are similar to those of assemblies 10, 14 and 12, respectively, of the analyzer of FIG. 1. Because of the improved structural features incorporated therein, however, the analyzer of FIG. 2 provides results which are significantly better than those of the analyzer of FIG. 1. The nature of these features, and the manner in which they produce these results, will now be described.

In accordance with one important feature of the present invention, source assembly 42 of FIG. 2 includes a reflecting element 48 having a concave annular reflecting surface 48a which lies in a surface of revolution that is centered on an axis 48b. As is more easily seen in FIG. 3, surface 48a lies in a surface of revolution which is generated by the rotation, about a central axis 48b, of a concave, preferably parabolic, figure having an axis 48c which is offset from central axis 48b by radial distance R. Because each cross-section of figure of revolution 48a includes segments of two parabolas, the reflective surface of element 48 has a focal region each point of which lies on a circle having a radius equal to R. As a result, all of the infrared radiation which is emitted by a heating element that lies exactly on this circle, and which is reflected from surface 48a, will emerge from the source assembly as a beam which is parallel to central axis 48b. Thus, to the extent that source assembly 42 meets the just stated condition, it will emit a beam of radiation which has an on-axis (or collimated) component that is large in relation to its off-axis (or non-collimated) component.

The above-described property of reflecting surface 48a is employed to advantage by including in source assembly 42 a heating element 50 which is circular, which has a radius equal to R and which substantially coincides with the focal region of reflecting surface 48a. The meeting of these requirements is assured by forming heating element 50 into a compact circular coil of radius R, and then attaching the leads thereof to lead mounting elements 50a and 50b which are provided with suitable insulating sleeves 52a and 52b. The resulting subassembly may then be mounted within reflecting element 48 by securing sleeves 52a and 52b in place within respective holes through element 48.

One advantage of the source assembly of the invention is that, because its heating element has a greater radius of curvature than the heating elements of the prior art, it can emit the desired quantity of infrared radiation with a smaller number of turns. Because of this smaller number of turns, the heating element of the invention can be made more compact and therefore more accurately coincident with the focal region of its reflective surface than the heating elements of the prior art. This, in turn, causes the source assembly of the invention to generate a beam with a higher degree of collimation than the beams generated by the source assemblies of the prior art.

Another advantage of the source assembly of the invention is that its heating element has a total radiating surface area which is greater than that of the heating elements of the prior art. As a result, its heating element can emit more radiation than previously used heating elements, without operating at a higher temperature. (Alternatively, the heating element of the invention can emit the same radiation as known heating elements while operating at a lower temperature.) This increased radiation output, in turn, improves both the sensitivity of the analyzer and its signal-to-noise ratio. This improvement will be understood to be in addition to that resulting from the previously mentioned improvement in the collimation of the infrared beam.

Figure 3:
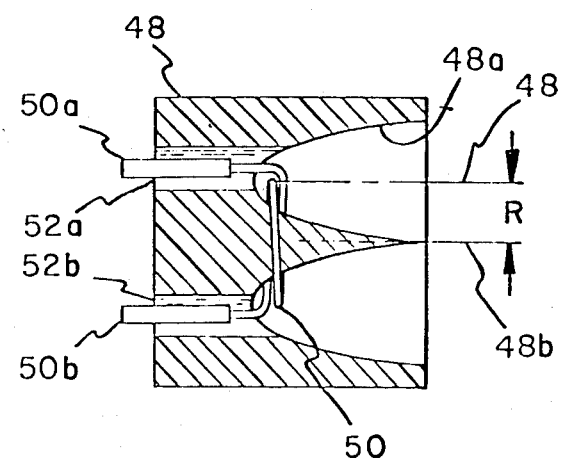
FIGS. 3 and 4 are cross-sectional and front views of the source assembly of the analyzer of FIG. 2,.
Figure 4:
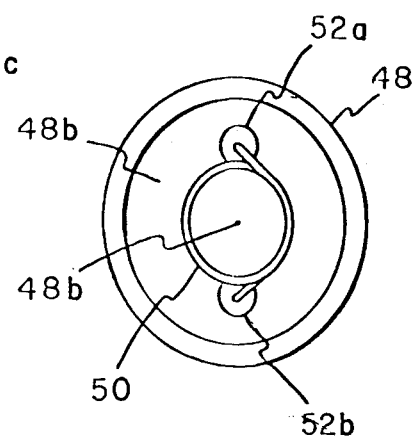
Figure 5:
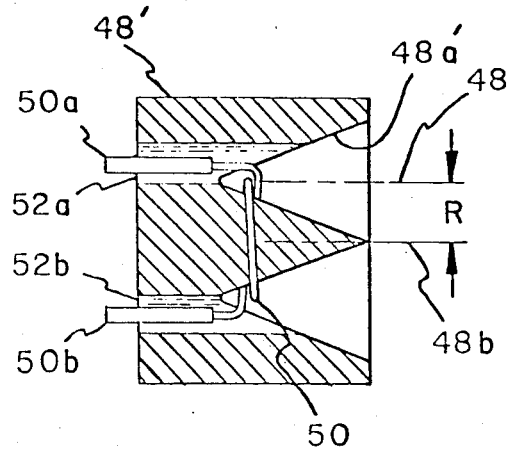
FIGS. 5 and 7 are cross-sectional and front views of an alternate source assembly which may be used in the analyzer of FIG. 2, FIGS. 8 and 9 are side and front elevational views of a part of the detecting assembly of the analyzer of FIG. 2.
Figure 7:
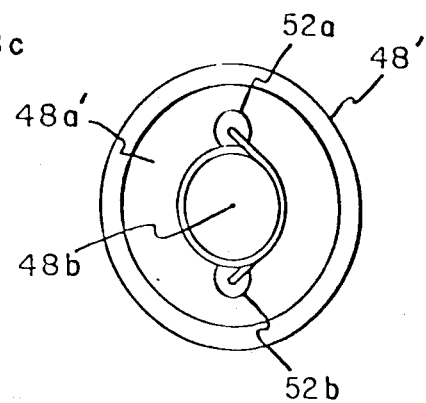

In the event that a degree of collimation which is less than that provided by a parabolic figure of revolution can be accepted in the interest of achieving a simpler source assembly geometry, the reflecting element of FIGS. 3 and 4 may be replaced by a reflecting element such as that shown in FIGS. 5 and 7. The latter reflecting element is generally similar to that of FIGS. 3 and 4, except that its reflecting surface 48a' lies in a surface of revolution which is generated by the revolution of an offset concave figure having a conic cross-section, rather than an offset conave figure having a parabolic cross-section. One disadvantage of the source assembly of FIGS. 5 and 7 is that the equivalent of the focal region of surface 48' (i.e., the heating element position which gives the optimum degree of beam collimation) will be dependent upon steepness of the conic figure, the length of the sample cell, etc., and must be determined on an empirical basis. It will be understood that the present invention contemplates other potential concave figures, such as those having circular, elliptical, hyperbolic, etc., cross-sections.

Because of the increased intensity and improved collimation of the infrared beam produced by source assembly 42, body 46 of cell assembly 44 need not have a reflective inner surface of the type which was necessary in previously used cell assemblies. This is because the desired high level of radiation transmission through the cell assembly does not rely upon multiple reflections of the off-axis components of the beam from the inner surface of the cell, but rather upon the increased intensity of the on-axis component of the beam that is generated by improved source assembly 42.

One advantage of using a cell body which does not have a reflective inner surface is the avoidance of the high cost of polishing and plating that inner surface. An even more important advantage is that the elimination of the reflective inner surface makes the output of the analyzer less dependent upon the off-axis component of the infrared beam. This reduced reliance upon off-axis component of the beam is beneficial because it reduces the tendency of the analyzer output to decrease with time as the flow of the sample gas deposits dirt on the inner surface of the cell body. As a result, the output of the analyzer of the invention is more stable, i.e., less subject to drift, than that of previously used analyzers.

While the combination of improved source assembly 42 with a cell body having an unpolished inner surface is used in the preferred embodiment of the invention, it is not an essential feature thereof. Accordingly, if it is necessary to use an infrared beam of the highest possible intensity, and if the deposition of dirt by the sample gas is not an important factor, cell body 46 of FIG. 2 may be replaced by a cell body of the type described in connection with FIG. 1.

In order to obtain the maximum benefit from the use of improved source assembly 42, detecting assembly 46 of the analyzer of FIG. 2 includes a number of improved features which assure the efficient collection and utilization of the infrared beam that emerges from cell assembly 44. One of these features is a detector housing 51 which is adapted to mount one or more solid-state detecting elements so that substantially all of the infrared radiation that is received by the detecting assembly may fall thereon. Another of these features is an improved reflecting element for efficiently concentrating the received infrared radiation on to the active parts of the detecting elements. Together with improved source assembly 42, improved detecting assembly 46 assures that the analyzer as a whole makes the most efficient possible use of the available infrared radiation, and thereby exhibits the maximum possible sensitivity and signal-to-noise ratio.

To the end that the above described results may be achieved, detecting assembly 46 is provided with a reflecting element 53 which includes first and second reflecting surfaces 53a and 53b. These surfaces serve to focus the on-axis component of the received infrared beam onto detecting elements 54 and 56, which are mounted in respective openings in detector housing 50. As will be explained more fully presently, the distances and angles between reflecting surfaces 53a and 53b, and detecting elements 54 and 56 are selected so that one half of the infrared beam is focused onto the end of detecting element 54 and the other half of the incident beam is focused onto the end of detecting element 56.

Figure 8:
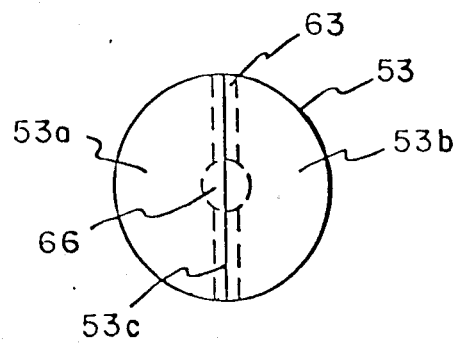
Figure 9:
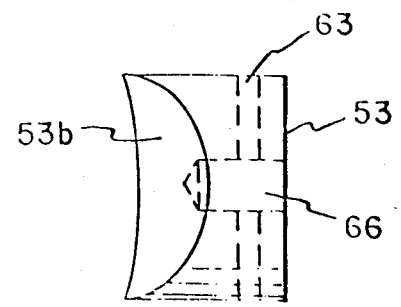

In order to assure that substantially all of the on-axis component of the infrared beam can be measured by detecting elements 54 and 56, reflecting surfaces 53a and 53b preferably comprise sections of paraboloids which have axes that are parallel to but offset from the longtitudinal axis of cell assembly 44, and which have foci that coincide with the active parts (usually the ends) of detecting elements 54 and 56. As is best seen in FIGS. 8 and 9, reflecting surfaces 53a and 53b each occupy one half of the field of view of the infrared beam that emerges from cell assembly 44. As a result, except for the infinitesimal amount of radiation that is scattered by the intersection 53c of surfaces 53a and 53b, the entire on-axis component of the infrared beam is focused directly onto detecting elements 54 and 56. Significantly, the received infrared beam is focused onto detecting elements 54 and 56 without encountering a radiation blocking structure such as the mounting for detecting elements 34 and 36 of FIG. 1. Since such mountings can block 10% or more of the total infrared beam, the elimination of this blocking structure significantly increases the magnitude of the output signals that are produced by detecting elements 54 and 56 for any given intensity of received infrared radiation. Improved detecting assembly 46 will therefore be seen to take full advantage of the increased intensity and collimation of the beam produced by improved source assembly 42.

In order to fully realize the above-described benefits, it is necessary that the spacing and orientation between reflecting surfaces 53a and 53b and detecting elements 54 and 56 be fixed with a high degree of accuracy. In the preferred embodiment this spacing and orientation is assured by using a detector housing 51 which includes a plurality of mounting and alignment holes 58 and 60 that fix the desired positions of detecting elements 54 and 56, and a plurality of mounting and alignment holes 62 and 64 that fix the desired positions of reflecting surfaces 53a and 53b.

During assembly, reflecting element 53 is pushed into hole 62 and then positioned so that hole 63 therethrough becomes aligned with hole 64 of housing 51. A locking pin (not shown) is then inserted into the holes 63 and 64 to hold reflecting element 53 in the precise position shown. During the positioning process, a hole 66 which has been drilled into reflecting element 53 for machining purposes, may be utilized to make any necessary adjustments in the position and orientation of element 53.

The fabrication of detecting assembly 46 is completed by securing detecting elements 54 and 56 in mounting holes 58 and 60, respectively. The desired insertion depth for elements 54 and 56 may be assured by providing holes 58 and 60 with suitable shoulders 66 and 68 which are adapted to engage the flanges that form parts of the metal cases thereof. When detecting elements 54 and 56 have been secured in holes 58 and 60 they will have the desired spacing and orientation with respect to reflecting surfaces 53a and 53b.

During the operation of the analyzer, the output signals of detecting elements 54 and 56 may be applied to a conventional signal processing circuit (not shown) for processing into an output signal that is suitable for application to a human-readable display. One of the detecting elements may, for example, be used as a reference (wideband) detector to provide a signal that is indicative of the total infrared output power of the source assembly, while the other is utilized as a measuring (narrow band) detector to provide a signal that is indicative of the concentration of the component of interest in the sample cell. The difference between the bandwidths of the two detectors may be produced by inserting in front of the measuring detector an infrared band pass filter having a pass band which coincides with one of the known absorption bands of the component of interest. Since signal processing circuits and band pass filters that are suitable for producing these results are known in the art, they will not be described in detail herein.

While the preferred embodiment of the present invention uses a detecting assembly that includes two solid-state infrared detecting elements, it is not restricted to use with such elements. An analyzer constructed in accordance with the invention may, for example, include a detecting assembly with more or less than two solid-state detecting elements, or with one or more other types of infrared detecting elements such as Luft-type detectors. One example of an analyzer that includes a detecting assembly of the latter type is shown in FIG. 6.

Referring to FIG. 6, there is shown a simplified cross-sectional view of an analyzer which includes source and cell assemblies that are the same as those shown in FIG. 2, but which includes a detecting assembly 70 that has both solid-state and Luft-type infrared detecting elements. More particularly, detecting subassembly 70 includes a first infrared assembly 46' which is similar to detecting assembly 46 of FIG. 2, except that it has only one solid-state detecting element 56 and a reflecting element 53' with only one reflecting surface 53b'. Detecting assembly 70 also includes a Luft-type detector 72 which may be a conventional "see-through" type detector that is charged with a known concentration of the component of interest. The term "see-through" refers to the fact that detector 70 includes a gas filled chamber 74 through which infrared radiation may pass via suitable infrared transparent windows 80 and 82.

Luft detector 72 operates in a conventional manner to selectively absorb a known fraction of the infrared radiation which is not absorbed by the component of interest during its transmission through the sample cell. As this occurs, the pressure of gas in upper chamber 74 changes, causing the position of a movable electrode 76 to change with respect to a fixed electrode 78. The resulting change in the capacitance between electrodes 76 and 78 is then used as an indication of the quantity of the component of interest within cell assembly 44. Because the use of Luft detectors is known in the art, the operation thereof will not be discussed in detail herein.

Because Luft detectors absorb infrared radiation only at specific wavelengths that are characteristic of the filling gas, most of the infrared radiation that is incident thereon passes therethrough substantially unattenuated. The latter radiation is therefore incident upon detecting subassembly 46' where it is concentrated by reflecting element 52b' and measured by solid-state detecting element 56. This, in turn, allows the output of detecting element 56 to be used as a signal to which the output of Luft detector 72 may be referenced for measurement purposes.

Because Luft detectors are more sensitive than solid-state detectors, the analyzer of FIG. 5 can be utilized to measure lower concentrations of a component of interest than the analyzer of FIG. 2. This enhanced sensitivity is, however, provided in conjunction with all of the previously described benefits of using the source and detecting assemblies of the invention. It therefore illustrates the previously stated fact the present invention may be used in analyzers having a variety of different configurations.

In view of the foregoing, it will be seen that the present invention contemplates an infrared analyzer which includes a number of improvements over previously known analyzers. Firstly, the analyzer includes a source assembly having improved reflecting and heating elements which together provide a more intense and more highly collimated beam of infrared radiation. Secondly, the analyzer includes a detecting assembly having an improved reflecting element which assures that substantially none of the on-axis component of the received infrared radiation is blocked or scattered. Finally, the invention makes possible the use of sample cells which have non-reflective inner surfaces, thereby improving the stability of the analyzer's output signal.

What is claimed is:

1. An infrared analyzer comprising:
   (a) a sample cell for conducting a flow of a sample gas, said cell comprising a chamber within which the sample gas may be illuminated by a beam of infrared radiation,
   (b) an infrared source assembly including:
      (i) a reflecting element, said reflecting element having a reflecting surface which lies in the surface of revolution formed by the rotation of a concave figure about an axis that is offset from the axis of the sample cell, and
      (ii) an approximately circular heating element mounted approximately at the focal region of the reflecting surface,
   (c) an infrared detecting assembly for receiving infrared radiation from the source assembly, through the sample cell, and converting said radiation into an electrical signal indicative of the composition of the sample gas.

2. The analyzer of claim 1 in which the sample cell has a generally non-reflective inner surface.

3. The analyzer of claim 1 in which the sample cell is composed of a plastic material which does not react chemically with the sample gas.

4. The analyzer of claim 1 in which said concave figure is a parabola, and in which said offset is approximately equal to the radius of the heating element.

5. The analyzer of claim 1 in which the detecting assembly includes a solid-state infrared detecting element and a reflecting element for focusing infrared radiation on the detecting element.

6. The analyzer of claim 5 in which the detecting element is located in a position in which it does not block the transmission of infrared radiation from the source assembly to the detecting assembly.

7. The analyzer of claim 1 in which the detecting assembly includes a plurality of detecting elements and a reflecting element, said reflecting element having a plurality of reflecting surfaces for focusing infrared radiation on respective detecting elements.

8. The analyzer of claim 7 in which the detecting assembly includes two detecting elements, and in which the reflecting surfaces of the reflecting element each comprise an off-axis section of a paraboloid.

9. The analyzer of claim 5 including a see-through Luft-type detector located between the sample cell and the detecting assembly.

10. The analyzer of claim 9 in which the Luft-type detector serves as a measuring detector and in which the solid-state detecting element serves as a reference detector.

11. An infrared analyzer comprising:
    (a) an infrared source assembly including:
       (i) an approximately circular heating element, and
       (ii) a reflecting element having a reflecting surface that includes an off-axis section of a parabola of revolution and an approximately circular focal region, said heating element substantially coinciding with said focal region, whereby the source assembly produces an approximately collimated beam of infrared radiation,
    (b) a sample cell for conducting a flow of a sample gas, said sample cell having an elongated body with a central axis that is aligned with said beam,
    (c) an infrared detecting assembly for receiving infrared radiation from the source assembly, through the sample cell, and converting said radiation into an electrical signal indicative of the composition of the sample gas.

12. The analyzer of claim 11 in which the sample cell has an unpolished inner surface.

13. The analyzer of claim 11 in which the sample cell is composed of a plastic which does not react chemically with the sample gas.

14. The analyzer of claim 11 in which the detecting assembly includes an infrared detecting element, and an infrared reflecting element having a reflecting surface for focusing infrared radiation onto the detecting element.

15. The analyzer of claim 14 in which the detecting element does not block the transmission of infrared radiation from the sample cell to the reflecting surface.

16. The analyzer of claim 11 in which the detecting assembly includes a plurality of solid-state infrared detecting elements, and in which the reflecting element includes a plurality of reflective surfaces for focusing infrared radiation onto respective detecting elements.

17. The analyzer of claim 16 in which each of said reflective surfaces includes an off-axis section of a paraboloid.

18. The analyzer of claim 14 including at least one see-through Luft-type detector located between the sample cell and the detecting assembly, in which said detecting element serves as a reference detector and the see-through Luft-type detector serves as a measuring detector.

19. The analyzer of claim 17 in which one of the detecting elements serves as a reference detector and another of the detecting elements serves as a measuring detector.

20. An infrared analyzer comprising:
    (a) a sample cell for conducting a flow of a sample gas, said sample cell comprising an elongated chamber having a generally non-reflective inner surface which is substantially parallel to the longitudinal axis thereof,
    (b) an infrared source assembly including:

(i) an approximately planar heating element, that is aligned with the longitudinal axis of the sample cell, said reflecting element having a surface cross-section which includes portions of two parabolas having axes that are parallel to but offset from said central axis, and (iii) means for mounting the heating element in the focal region of said surface, (c) an infrared detecting assembly for receiving radiation from the source assembly, through the sample cell, and converting said radiation to an electrical signal indicative of the composition of the sample gas.

21. The analyzer of claim 20 in which the heating element is generally circular and substantially coincides with the focal region of said reflecting surface.

22. The analyzer of claim 20 in which the detecting assembly includes a solid-state infrared detecting element, and an infrared reflecting element for focusing radiation thereon.

23. The analyzer of claim 22 in which the detecting element does not lie in the field of view of the reflecting element.

24. The analyzer of claim 20 in which the detecting assembly includes a plurality of solid-state infrared detecting elements, and in which the reflecting element includes a plurality of reflective surfaces for focusing infrared radiation onto respective detecting elements.

25. The analyzer of claim 24 in which said reflective surfaces comprise sections of off-axis paraboloids.

26. The analyzer of claim 22 including at least one see-through Luft-type detector located between the sample cell and the detecting assembly, in which the solid-state detecting element serves as a reference detector and the see-through Luft-type detector serves as a measuring detector.

27. The analyzer of claim 24 in which one of the detecting elements serves as a reference detector and another of the detecting elements serves as a measuring detector.

* * * * *

UNITED STATES PATENT AND TRADEMARK OFFICE
CERTIFICATE OF CORRECTION

PATENT NO. : 4,618,771

DATED : October 21, 1986

INVENTOR(S) : Carl A. Farren

It is certified that error appears in the above—identified patent and that said Letters Patent is hereby corrected as shown below:

Claim 20, Column 11, line 1, after "element," delete -- that is --;

Claim 20, Column 11, line 2, begin a new subparagraph b (ii);

Claim 20, Column 11, line 2, before "aligned" insert -- (ii) a reflecting element having a central axis that is --.

Signed and Sealed this

Sixth Day of January, 1987

Attest:

Attesting Officer

DONALD J. QUIGG

Commissioner of Patents and Trademarks